United States Patent [19]

Hanko et al.

[11] Patent Number: 5,254,543

[45] Date of Patent: Oct. 19, 1993

[54] SULPHONYLBENZYL-SUBSTITUTED PYRIDONES WHICH ARE ANGIOTENSION II RECEPTOR ANTAGONISTS

[75] Inventors: Rudolf Hanko, Duesseldorf; Walter Hübsch, Wuppertal; Jürgen Dressel, Wuppertal; Peter Fey, Wuppertal; Thomas Krämer, Wuppertal; Ulrich Müller, Wuppertal; Matthias Müller-Gliemann, Solingen-Ohligs; Martin Beuck, Erkrath; Stanislav Kazda; Claudia Hirth-Dietrich, both of Wuppertal; Andreas Knorr, Erkrath; Johannes-Peter Stasch, Wuppertal; Stefan Wohlfeil, Hilden; Özkan Yalkinoglu, Wuppertal, all of Fed. Rep. of Germany

[73] Assignee: Bayer Aktiengesellschaft, Leverkusen, Fed. Rep. of Germany

[21] Appl. No.: 19,000

[22] Filed: Feb. 18, 1993

[30] Foreign Application Priority Data

Feb. 27, 1992 [DE] Fed. Rep. of Germany ....... 4206045

[51] Int. Cl.$^5$ ................... A61K 31/44; C07D 401/10
[52] U.S. Cl. .................... 514/89; 514/235.5; 514/333; 514/335; 514/343; 544/131; 546/21; 546/275; 546/276; 546/281
[58] Field of Search ............... 546/275, 276, 281, 21; 544/131; 514/89, 235.5, 333, 335, 343

[56] References Cited

U.S. PATENT DOCUMENTS

| 5,128,355 | 7/1992 | Carini et al. | 514/381 |
| 5,138,069 | 10/1992 | Carini et al. | 548/252 |
| 5,153,197 | 10/1992 | Carini et al. | 514/255 |
| 5,155,118 | 10/1992 | Carini et al. | 514/381 |

FOREIGN PATENT DOCUMENTS

| 0403158 | 12/1990 | European Pat. Off. . |
| 0403159 | 12/1990 | European Pat. Off. . |
| 0425211 | 5/1991 | European Pat. Off. . |
| 0487745 | 12/1991 | European Pat. Off. . |
| 3406329 | 8/1985 | Fed. Rep. of Germany . |
| 91/00281 | 1/1991 | PCT Int'l Appl. . |

OTHER PUBLICATIONS

E. L. Eliel, Stereochemistry of Carbon Compounds, McGraw Hill, 1962 (this citation encompasses a whole book).
J. C. Sheehand, S. L. Ledis, J. Am. Chem. Soc. 95, 875 (1973).
Frerman et al., J. Biol. Chem. 225, 7087–7093 (1983).
N. B. Benoiton, K. Kluroda, Int. J. Pept. Prot. Res. 17, 197–204 (1981).
R. P. Mariella, R. Stansfield, J. Am. Chem, Soc 73, 1368 (1951).
O. Isler et al., Helv. Chim. Acta 38, 1033 (1955).
Bull. Soc. Chim. Fra. 687 (1958).

Primary Examiner—Bernard Dentz
Attorney, Agent, or Firm—Sprung Horn Kramer & Woods

[57] ABSTRACT

Sulphonylbenzyl-substituted pyridones can be prepared by reacting pyridones with sulphonylbenzyl compounds. The sulphonylbenzyl-substituted pyridones can be employed as active compounds in medicaments, in particular for the treatment of arterial hypertension and atherosclerosis.

7 Claims, No Drawings

SULPHONYLBENZYL-SUBSTITUTED PYRIDONES WHICH ARE ANGIOTENSION II RECEPTOR ANTAGONISTS

The present invention relates to sulphonylbenzyl-substituted pyridones, to a process for their preparation and to their use in medicaments, in particular as hypotensive and anti-atherosclerotic agents.

It is known that renin, a proteolytic enzyme, degrades the decapeptide angiotensin I, which is in turn degraded in the lungs, the kidneys or other tissues to the hypertensive octapeptide angiotensin II, from angiotensinogen in vivo. The various effects of angiotensin II, such as, for example, vasoconstriction, Na+ retention in the kidneys, aldosterone release in the adrenal gland and an increase in tone of the sympathetic nervous system act synergistically in the sense of a blood pressure increase.

Moreover, angiotensin II has the property of promoting the growth and the replication of cells such as, for example, heart muscle cells and smooth muscle cells, these growing and proliferating in an increased manner in various disease states (for example hypertension, atherosclerosis and cardiac insufficiency).

A possible starting point for intervention in the renin-angiotensin system (RAS) is, in addition to the inhibition of renin activity, the inhibition of the activity of angiotensin converting enzyme (ACE) and the blockade of angiotensin II receptors.

The present invention relates to sulphonylbenzyl-substituted pyridones of the general formula (I)

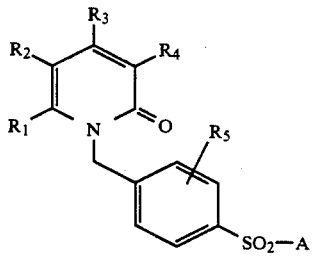

in which
R$^1$ represents straight-chain or branched alkyl having up to 8 carbon atoms, which is optionally substituted by cycloalkyl having 3 to 6 carbon atoms, hydroxyl or by straight-chain or branched alkoxy having up to 6 carbon atoms, or represents cycloalkyl having 3 to 6 carbon atoms,
R$^2$, R$^3$ and R$^4$ are identical or different and represent hydrogen, cyano or straight-chain or branched perfluoroalkyl having up to 8 carbon atoms, or represent straight-chain or branched alkyl having up to 8 carbon atoms, which is optionally monosubstituted or disubstituted by identical or different substituents from the group consisting of hydroxyl, halogen, carboxyl, and straight-chain or branched alkoxy or alkoxycarbonyl each having up to 6 carbon atoms, or by phenyl, phenoxy or by a 5- to 7-membered, saturated or unsaturated heterocycle having up to three heteroatoms, where the cyclic systems can in turn be monosubstituted or disubstituted by identical or different substituents from the group consisting of trifluoromethyl, trifluoromethoxy, halogen, nitro, cyano, hydroxyl and hydroxymethyl or by straight-chain or branched alkyl or alkoxy each having up to 6 carbon atoms, or represent straight-chain or branched acyl or alkoxycarbonyl each having up to 8 carbon atoms, benzyloxycarbonyl or carboxyl, or represent phenyl which is optionally monosubstituted to trisubstituted by identical or different substitutents from the group consisting of halogen, nitro, cyano, hydroxyl, hydroxymethyl, trifluoromethyl and trifluoromethoxy or by straight-chain or branched alkyl or alkoxy each having up to 6 carbon atoms, or represent a group of the formula —CO—NR$^6$,R$^7$, in which
R$^6$ and R$^7$ are identical or different and denote hydrogen, straight-chain or branched alkyl having up to 8 carbon atoms or aryl or aralkyl each having 6 to 10 carbon atoms,
R$^5$ represents hydrogen, halogen or straight-chain or branched alkyl having up to 8 carbon atoms, or represents straight-chain or branched perfluoroalkyl having up to 6 carbon atoms, or represents a group of the formula —OX, wherein
X denotes hydrogen, benzyl, a hydroxyl protective group or denotes straight-chain or branched alkyl having up to 8 carbon atoms,
A represents a 3 to 8-membered saturated heterocycle bonded via the nitrogen atom and having up to 2 further heteroatoms from the series consisting of S, N and O and which is optionally monosubstituted or disubstituted by identical or different substituents from the group consisting of perfluoroalkyl having up to 5 carbon atoms and a radical of the formula

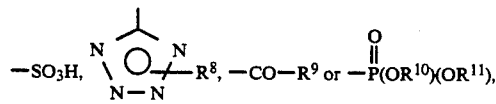

in which
R$^8$ denotes hydrogen, straight-chain or branched alkyl having up to 6 carbon atoms or triphenylmethyl
R$^9$ denotes hydroxyl, straight-chain or branched alkoxy having up to 8 carbon atoms, phenoxy, benzyloxy or a group of the formula —NR$^{12}$R$^{13}$, in which
R$^{12}$ and R$^{13}$ are identical or different and denote hydrogen or straight-chain or branched alkyl having up to 6 carbon atoms or phenyl,
R$^{10}$ and R$^{11}$ are identical or different and denote hydrogen, straight-chain or branched alkyl having up to 8 carbon atoms or phenyl,
and their salts.

The sulphonylbenzyl-substituted pyridones according to the invention can also be present in the form of their salts. In general, salts with organic or inorganic bases or acids may be mentioned here.

In the context of the present invention, physiologically acceptable salts are preferred. Physiologically acceptable salts of the sulphonylbenzyl-substituted pyridones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts and also ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, either as enantiomers or as diasteriomers. The invention relates both to the enantiomers or diastereomers and to their respective mixtures. Like the diastereomers, the racemic forms can also be separated in a known manner into the stereoisomerically uniform constituents [cf. E. L. Eliel, Stereochemistry of Carbon Compounds, McGraw Hill, 1962].

Heterocycle in the definitions of $R^2$, $R^3$ and $R^4$ in general represents a 5- to 7-membered, preferably 5- to 6-membered, saturated or unsaturated ring which as heteroatoms can contain up to 2 oxygen, sulphur and/or nitrogen atoms. 5- and 6-membered rings having one oxygen, sulphur and/or up to 2 nitrogen atoms are preferred. The following may preferably be mentioned: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

A 3- to 8-membered saturated heterocycle bonded via the nitrogen atom, which can additionally contain up to 2 oxygen, sulphur and/or nitrogen atoms as heteroatoms, in general represents azetidinyl, piperidyl, morpholinyl, piperazinyl or pyrrolidinyl. 5- and 6-membered rings having one oxygen and/or up to 2 nitrogen atoms, such as, for example, piperidyl, morpholinyl or pyrrolidinyl, are preferred. Pyperidyl and pyrrolidinyl are particularly preferred.

Preferred compounds of the general formula (I) are those in which $R^1$ represents a straight-chain or branched alkyl each having up to 6 carbon atoms, which is optionally substituted by cyclopropyl, cyclopentyl, cyclohexyl, hydroxyl or by straight-chain or branched alkoxy having up to 4 carbon atoms, or represents cyclopropyl, cyclopentyl or cyclohexyl, $R^2$, $R^3$ and $R^4$ are identical or different and represent hydrogen, cyano or straight-chain or branched perfluoroalkyl having up to 6 carbon atoms, or represent straight-chain or branched alkyl having up to 6 carbon atoms, which is substituted by hydroxyl, fluorine, chlorine, bromine, carboxyl, straight-chain or branched alkoxy or alkoxycarbonyl each having up to 4 carbon atoms, or by phenyl, phenoxy or thienyl, where the cyclic systems can in turn be substituted by trifluoromethoxy, trifluoromethyl, hydroxymethyl, fluorine, chlorine, bromine or by straight-chain or branched alkyl or alkoxy each having up to 6 carbon atoms, or represent straight-chain or branched acyl or alkoxycarbonyl each having up to 6 carbon atoms, benzyloxycarbonyl or carboxyl, or represent phenyl which is optionally monosubstituted or disubstituted by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula $-CONR^6R^7$, in which $R^6$ and $R^7$ are identical or different and denote hydrogen, straight-chain or branched alkyl having up to 6 carbon atoms, phenyl or benzyl, $R^5$ represents hydrogen, fluorine, chlorine, bromine, or straight-chain or branched alkyl having up to 6 carbon atoms, or represents straight-chain or branched perfluoroalkyl having up to 4 carbon atoms, or represents a group of the formula $-OX$, wherein X denotes hydrogen, benzyl, acetyl, or denotes straight-chain or branched alkyl having up to 6 carbon atoms, A represents piperidyl, pyrrolidinyl or morpholinyl bonded via the nitrogen atom, each of which is optionally substituted by trifluoromethyl or by a radical of the formula

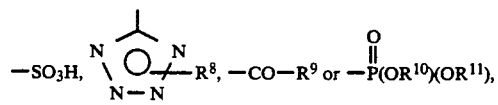

in which $R^8$ denotes hydrogen, straight-chain or branched alkyl having up to 4 carbon atoms or triphenylmethyl, $R^9$ denotes hydroxyl, straight-chain or branched alkoxy having up to 6 carbon atoms, phenoxy, benzyloxy or a group of the formula $-NR^{12}R^{13}$, in which $R^{12}$ and $R^{13}$ are identical or different and denote hydrogen or straight-chain or branched alkyl having up to 4 carbon atoms, $R^{10}$ and $R^{11}$ are identical or different and denote hydrogen, straight-chain or branched alkyl having up to 6 carbon atoms or phenyl, and their salts.

Particularly preferred compounds of the general formula (I) are those in which $R^1$ represents straight-chain or branched alkyl having up to 4 carbon atoms, which is optionally substituted by cyclopropyl or represents cyclopropyl, $R^2$, $R^3$ and $R^4$ are identical or different and represent hydrogen, cyano or straight-chain or branched perfluoroalkyl having up to 4 carbon atoms, represent straight-chain or branched alkyl having up to 4 carbon atoms, which is substituted by hydroxyl or straight-chain or branched alkoxy or alkoxycarbonyl each having up to 3 carbon atoms, or represent straight-chain or branched acyl or alkoxycarbonyl each having up to 4 carbon atoms, benzyloxycarbonyl or carboxyl, or represent a group of the formula $-CONR^6R^7$, in which $R^6$ and $R^7$ are identical or different and denote hydrogen, straight-chain or branched alkyl having up to 4 carbon atoms, phenyl or benzyl, $R^5$ represents hydrogen, fluorine, chlorine, straight-chain or branched alkyl having up to 4 carbon atoms, or represents straight-chain or branched perfluoroalkyl having up to 3 carbon atoms, or represents a group of the formula $-OX$, wherein X denotes hydrogen, benzyl, acetyl or denotes straight-chain or branched alkyl having up to 6 carbon atoms, A represents piperidyl or pyrrolidinyl bonded via the nitrogen atom, each of which is optionally substituted by trifluoromethyl or by a radical of the formula

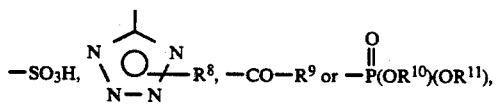

in which

R$^8$ denotes hydrogen, methyl, ethyl or triphenylmethyl,

R$^9$ denotes hydroxyl, straight-chain or branched alkoxy having up to 4 carbon atoms, phenoxy, benzyloxy or a group of the formula —NR$^{12}$R$^{13}$, in which R$^{12}$ and R$^{13}$ are identical or different and denote hydrogen or straight-chain or branched alkyl having up to 3 carbon atoms and R$^{10}$ and R$^{11}$ are identical or different and denote hydrogen, straight-chain or branched alkyl having up to 4 carbon atoms or phenyl, and their salts.

Additionally, a process for the preparation of the compounds of the general formula (I) according to the invention has been found, characterised in that pyridones of the general formula (II)

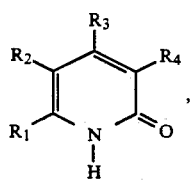
(II)

in which
R$^1$, R$^2$, R$^3$ and R$^4$ have the abovementioned meaning, are reacted with compounds of the general formula (III)

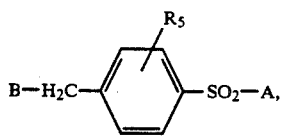
(III)

in which
R$^5$ and A have the abovementioned meaning and
B represents halogen, preferably bromine,
in organic solvents and in the presence of a base and if appropriate of a catalyst,
and in the case in which R$^8 \neq$ hydrogen an alkylation is added and in the case of the acids (R$^9$=OH) the corresponding esters are hydrolysed
and in the case of the esters or amides, if appropriate via an activated carboxylic acid step, an esterification or amidation is added
and the substituents R$^2$, R$^3$, R$^4$ and R$^5$ are varied by customary methods.

The process according to the invention can be illustrated by way of example by the following equation:

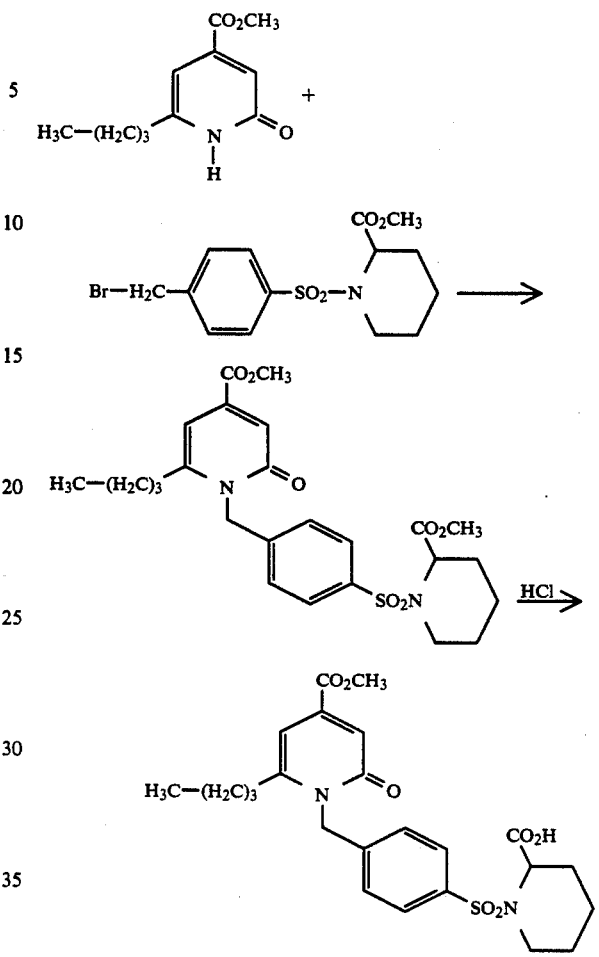

Suitable solvents for the process are the customary organic solvents which do not change under the reaction conditions. These preferably include ethers such as diethyl ether, dioxane, tetrahydrofuran, glycol dimethyl ether, 1,2-dimethoxyethane or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Tetrahydrofuran and 1,2-dimethoxyethane are preferred.

The bases which can be employed for the process according to the invention are in general inorganic or organic bases. These preferably include alkali metal hydroxides or alkaline earth metal hydroxides such as, for example, sodium hydroxide, potassium hydroxide or lithium hydroxide, barium hydroxide, alkali metal or alkaline earth metal carbonates such as sodium carbonate, potassium carbonate, calcium carbonate or caesium carbonate, or alkali metal or alkaline earth metal alkoxides such as sodium methoxide or potassium methoxide or potassium tert-butoxide, or lithium diisopropylamide (LDA), or organic amines (trialkyl(C$_1$-C$_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium or its hydrides such as sodium hydride, as bases. Potassium carbonate, sodium hydride, potassium tert-butoxide and caesium carbonate are preferred.

In general, the base is employed in an amount from 0.05 mol to 10 mol, preferably from 1 mol to 2 mol, relative to 1 mol of the compound of the formula (III).

The process according to the invention is in general carried out in a temperature range from −100° C. to +100° C., preferably from 0° C. to 40° C.

The process according to the invention is in general carried out at normal pressure. However, it is also possible to carry out the process at elevated pressure or at reduced pressure (for example in a range from 0.5 to 5 bar).

The removal of the triphenylmethyl group is carried out using acetic acid or trifluoroacetic acid and water or one of the abovementioned alcohols or using aqueous hydrochloric acid in the presence of acetone or also in alcohols.

The removal is in general carried out in a temperature range from 0° C. to 150° C., preferably from 20° C. to 100° C., and at normal pressure.

Suitable catalysts are potassium iodide or sodium iodide, preferably sodium iodide.

Alkylation is in general carried out using alkylating agents such as, for example, ($C_1$-$C_6$)alkyl halides, sulphonic acid esters or substituted or unsubstituted ($C_1$-$C_6$)-dialkyl or ($C_1$-$C_6$)-diaryl sulphonates, preferably methyl iodide or dimethyl sulphate.

Alkylation is in general carried out in one of the abovementioned solvents, preferably in dimethylformamide in a temperature range from 0° C. to +70° C., preferably from 0° C. to +30° C. and at normal pressure.

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Sodium hydroxide, potassium hydroxide or lithium hydroxide are particularly preferred.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned. Tetrahydrofuran and methanol are preferred.

The hydrolysis can optionally also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out using acids, such as, for example, hydrochloric acid or trifluoroacetic acid, in the presence of one of the abovementioned solvents and/or water or their mixtures, preferably using dioxane or tetrahydrofuran.

The amidation and the sulphonamidation are in general carried out in one of the abovementioned solvents, preferably in tetrahydrofuran or dichloromethane.

The amidation and the sulphonamidation can optionally proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from −20° C. to +80° C., preferably from −10° C. to +30° C. and at normal pressure.

Suitable bases for this purpose in addition to the abovementioned bases are preferably triethylamine and/or dimethylaminopyridine, DBU or DABCO.

The base is employed in an amount from 0.5 to 10 mol, preferably from 1 mol to 2 mol, relative to 1 mol of the corresponding acid or ester.

Acid-binding agents for the sulphonamidation which can be employed are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]-none-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. LEdis, J. Am. Chem. Soc. 95, 875 (1973); F. E. Frerman et al., J. Biol. Chem. 225, 507 (1982) and N. B. Benoton, K. Kluroda, Int. Pept. Prot. Res. 13, 403 (1979), 17, 187 (1981)].

The acid-binding agents and dehydrating reagents are in general employed in an amount from 0.5 to 3 mol, preferably from 1 to 1.5 mol, relative to 1 mol of the corresponding carboxylic acids.

The compounds of the general formula (II) are known in some cases [cf., for example, DE No. 3,406,329 A1, R. P. Mariella, R. Stansfield, J. Am. Chem. Soc. 73, 1368 (1951) and O. Isler et al., Helv. Chim. Acta 38, 1033 (1955) Bull. Soc. Chim. Fr. 687

(1958)] or are new and can then be prepared in methods analogous to those publications cited above.

The compounds of the general formula (III) are new and can be prepared by reacting substituted benzylsulphonyl chlorides of the general formula IV

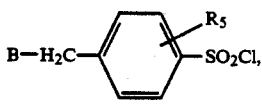

in which

B and $R^5$ have the abovementioned meaning, with compounds of the general formula (V)

$$H-A \qquad (V),$$

in which

A has the abovementioned meaning, in one of the abovementioned solvents and bases, preferably in dichloromethane, using triethylamine.

In general, the reaction is carried out at normal pressure. However, it is also possible to work at reduced pressure or at elevated pressure (for example from 0.5 to 5 bar).

When carrying out the reaction, the base is in general employed in an amount from 1 to 3 mol, preferably from 1 to 1.5 mol, relative to 1 mol of the compounds of the general formula (IV). Molar amounts of the reactants are particularly preferably used.

The reaction is in general carried out in a temperature range from $-40°$ C. to $+40°$ C., preferably from $-30°$ C. to $0°$ C. and at normal pressure.

The compounds of the general formulae (IV) and (V) are known or can be prepared by a customary method.

The compounds of the general formula (I) according to the invention show an unforseeable, useful spectrum of pharmacological action.

The compounds according to the invention have a specific A II-antagonistic action, since they inhibit the binding of angiotensin II to A II receptors. They suppress the vasoconstrictor and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, brain function disorders, ischaemic brain diseases, peripheral circulatory disorders, functional disorders of the kidney and adrenal gland, bronchospastic diseases and diseases of the respiratory tract having a vascular cause, sodium retention and oedemas.

Moreover, the substances have a natriuretic and diuretic effect. This effect shows itself in a mobilisation of oedema fluid during pathological fluid increase of cardiac and non-cardiac origin.

Investigation of the Inhibition of the Agonist-induced Contraction

Rabbits of both sexes are stunned by a blow to the neck and bled out, or in some cases anesthetised with Nembutal (about 60–80 mg/kg i.v.) and sacrificed by opening the thorax. The thorax aorta is taken out, freed from adhering connective tissue, divided into 1.5 mm wide ring segments and individually transferred under an initial loading of about 3.5 g to 10 ml organ baths containing 95% $O_2$/5% $CO_2$-aerated Krebs-Henseleit nutrient solution temperature-controlled at 37° C. of the following composition: 119 mmol/l of NaCl; 2.5 mmol/l of $CaCl_2 \times 2$ $H_2O$; 1.2 mmol/l of $KH_2PO_4$; 10 mmol/l of glucose; 4.8 mmol/l of KCl; 1.4 mmol/l of $MgSO_4 \times 7$ $H_2O$ and 25 mmol/l of $NaHCO_3$.

The contractions are measured isometrically by Statham UC2 cells by means of bridge amplifiers (ifd Mulheim or DSM Aalen) and digitalised and analysed by means of A/D convertors (System 570, Keithley Munich). Agonist dose response curves (DRC) were plotted hourly. With each DRC, 3 or 4 individual concentrations are applied to the baths at an interval of 4 min. After completion of the DRC and subsequent washing-out cycles (16 times, in each case about 5 sec/min with the abovementioned nutrient solution), a 28-minute resting or incubation phase is added in the course of which the contractions reach the starting value again.

The height of the 3rd DRC in the normal case is used as a reference quantity for the evaluation of the test substance to be investigated in further passages, which is applied to the baths in the following DRCs in increasing dosage in each case at the start of the incubation time. In this way, each aorta ring is always stimulated for the whole day with the same agonist.

Agonists and their standard concentrations (Administration volume per individual dose=100 µl):

| | | |
|---|---|---|
| KCl | 22.7; 32.7; 42.7; 52.7 | mmol/l |
| l-noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

To calculate the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

TABLE A

Inhibition of vascular contraction in isolated rabbit aorta rings in vitro
$IC_{50}$ (nM) against contractions induced by:

| Ex. No.: | AII |
|---|---|
| 6 | 280 |

Blood Pressure Measurements on the Angiotensin II-infused Rat

Male Wistar rats (Moellegaard, Copenhagen, Denmark) having a body weight of 300–350 g are anaesthetised with Thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglion blocker pentolinium (5 mg/kg i.v.), the angiotensin II infusion is started (0.3 µg/kg/min). As soon as the blood pressure values have reached a stable plateau, the test substances are administered either intravenously or as a suspension or solution in 0.5%

Tylose. The blood pressure changes under the effect of the substance are given in the table as average values ±SEM.

Determination of Anti-hypertensive Activity in Conscious Hypertensive Rats

The oral antihypertensive activity of the compounds according to the invention was tested on conscious rats having a surgically induced unilateral renal artery stenosis. To do this, the right renal artery was constricted with a silver clip of 0.18 mm internal width. In this type of hypertension, the plasma renin activity increases in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

Additionally, the compounds according to the invention inhibit the specific binding of radioactive angiotensin II in a concentration-dependent manner.

Interaction of the Compounds According to the Invention with the Angiotensin II Receptor on Membrane Fractions of Adrenal Gland Vortex (Bovine)

Bovine adrenal gland cortices (AGC) which have been freshly removed and carefully freed from gland medulla are comminuted in sucrose solution (0.32M) with the aid of an Ultra-Turrax (Janke & Kunkel, Staufen i.B.) to give a coarse membrane homogenate and are partially purified to give membrane fractions in two centrifugation steps. The receptor binding investigations are carried out on partially purified membrane fractions of bovine AGC using radioactive angiotensin II in an assay volume of 0.25 ml which, in detail, contains the partially purified membranes (50–80 $\mu$g) $^3$H-angiotensin II (3–5 nM), test buffer solution (50 mM tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ or $IC_{50}$ values ($K_i$:$IC_{50}$ values corrected for the radioactivity used; $IC_{50}$ values: concentration at which the substance to be investigated causes a 50% inhibition of the specific binding of the radioligand).

Investigation of the Inhibition of Proliferation of Smooth Muscle Cells by the Compounds According to the Invention To determine the antiproliferative action of the compounds, smooth muscle cells are used which have been obtained from the aortas of rats or pigs by the media explant technique [R. Ross, J. Cell. Biol. 50, 172, 1971]. The cells are innoculated into suitable culture dishes, as a rule 24-hole plates, and cultured at 37° C. for 2-3 days in medium 199 containing 7.5% FCS and 7.5% NCS, 2 mM L-glutamine and 15 mM HEPES, pH 7.4 in 5% $CO_2$. The cells are then synchronised by withdrawal of serum for 2-3 days and then stimulated into growth with AII, serum or other factors. Test compounds are simultaneously added. After 16-20 hours, 1 $\mu$Ci of $^3$H-thymidine is added and, after a further 4 hours, the incorporation of this substance into the TCA-precipitatable DNA of the cells is determined.

Test for Natriuretic Effect

Fasting Wistar rats are treated orally with test substance (suspended in Tylose solution). The urine excretion is then collected in diuresis cages over the course of 6 hours. The concentration of sodium and potassium in the urine is determined by flame photometry.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to deviate from the amounts mentioned, in particular depending on the body weight or the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

Solvents:
a = $CH_2Cl_2/CH_3/OH = 10:1$
b = $CH_2Cl_2/CH_3OH/CH_3CO_2H = 10:1:0.5$
c = $CH_2Cl_2/CH_3OH = 5:1$

Starting Compounds

Example I

6-Butyl-4-methoxycarbonyl-2-oxo-1,2-dihydropyridine

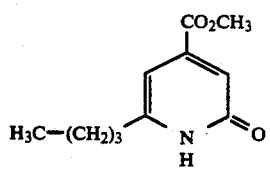

12.5 ml (0.17 mol) of thionyl chloride are added dropwise with ice-cooling to a suspension of 29.25 g (0.15 mol) of 6-butyl-2-oxo-1,2-dihydro-isonicotinic acid in 200 ml of methanol and the mixture is stirred overnight at room temperature. It is concentrated to dryness and the residue is chromatographed on 450 g of silica gel (230–400 mesh) using dichloromethane dichloromethane/methanol 10:1. 29.6 g (94%) of colourless crystals of melting point 106° C. crystallised from dichloromethane, ether and petroleum ether.

Example II

6-Butyl-pyrid-2(1H)-one

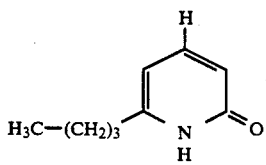

4.9 g (25 mmol) of 6-butyl-2-oxo-1,2-dihydro-isonicotinic acid are refluxed for 1.5 h with 1.79 g (12.5 mmol) of copper(I) oxide in 50 ml of quinoline (237° C). After filtering off, the volatile constituents are removed by distillation in vacuo (110° C. at 17 mbar, then 67° C. at 9 mbar). The residue is chromatographed twice on silica gel using dichloromethane/methanol (40:1) → (20:1) and the product is stirred in petroleum ether.

Yield: 1.95 g (52%) of brownish crystals of melting point 68° C.

Example III 4-(Bromomethyl)benzene-sulphochloride

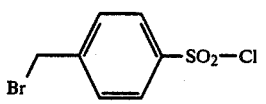

38.1 g (0.2 mol) of 4-methylbenzenesulphonyl chloride are dissolved in 300 ml of carbon tetrachloride and treated with 35.6 g (0.2 mol) of N-bromosuccinimide and, after addition of 0.2 g (1.2 mmol) of azobisisobutyronitrile (ABU), the mixture is heated under reflux for 4 h. After cooling, the solids are filtered off and the filtrate is freed from the solvent. Flash chromatography (petroleum ether/toluene 4:1, 50 μm particle size) and subsequent recrystallisation from 100 ml of cyclohexane gives 24.0 g (45% of theory) of the title compound.
$R_f$=0.75 (toluene)

Example IV 4-(Bromomethyl)-3-chlorobenzenesulphochloride

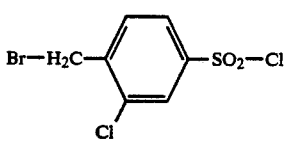

45.9 g (0.2 mol) of sodium 3-chloro-4-methylbenzenesulphonate are mixed with 83.3 g (0.4 mol) of phosphorus pentachloride and heated for 30 min at an oil bath temperature of 140° C. The hot mixture is treated with 500 ml of toluene, and the resulting solution is heated to boiling and, after cooling, poured onto ice. The organic phase is separated off and washed with water (2×200 ml). After drying over MgSO$_4$, it is filtered and all the volatiles are stripped off in vacuo. The residue obtained is purified by flash chromatography (petroleum ether/toluene 4:1, 50 μm particle size). 24.9 g of a product are obtained which is immediately reacted further:

It is taken up in 200 ml of carbon tetrachloride and, after addition of 19.6 g (0.11 mol) of N-bromosuccinimide and 0.1 g (0.6 mmol) of ABN, heated under reflux for 6 h. After cooling, the solids are filtered off and the filtrate is freed from solvent. Flash chromatography (petroleum ether/toluene 4:1, 50 μ particle size) gives 21.2 g (35%) of the title compound.

$R_f$=0.32 (petroleum ether/dichloromethane 4:1)

Example V 4-(Bromomethyl)-benzenesulphonyl-N-pyrrolidinide 5.3 g (0.02 mol) of the compound from Example III are dissolved in 200 ml of dichloromethane and 4.0 g (0.04 mol) of triethylamine and, after addition of 1.4 g (0.02 mol) of pyrrolidine, the mixture is stirred at 0° C. for 1 h in 50 ml of dichloromethane. The mixture is extracted with 2N HCl (2×100 ml), H$_2$O (2×100 ml), dried over MgSO$_4$ and filtered, and all the volatile components are evaporated in vacuo.

Yield: 5.4 g (89% of theory)
$R_f$=0.09 (toluene)

Example VI 4-(Bromomethyl)-benzenesulphonyl-N-piperidinide

In analogy to the procedure of Example V, 1.0 g (81% of theory) of the title compound is obtained from 1.1 g (4 mmol) of the compound from Example III and 0.34 g (4 mmol) of piperidine.

$R_f = 0.14$ (toluene)

Example VII (S)-4-(Bromomethyl)-benzenesulphonyl-N-2-(tert-butoxycarbonyl)pyrrolidinide

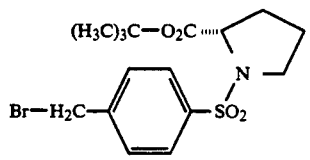

In analogy to the procedure of Example V, 9.1 g (84% of theory) of the title compound are obtained from 7.25 g (27 mmol) of the compound from Example III and 4.6 g (27 mmol) of S-proline tert-butyl ester.

$R_f = 0.66$ (petroleum ether/ethyl acetate 7:3)

Example VIII rac-4-(Bromomethyl)-benzenesulphonyl-N-2-(tert-butoxycarbonyl)piperidinide

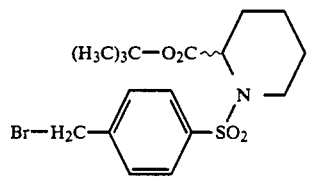

In analogy to the procedure of Example V, 7.4 g (59% of theory) of the title compound are obtained from 8.0 g (30 mmol) of the compound from Example III and 5.5 g (30 mmol) of tert-butyl rac-pipercolate.

$R_f = 0.53$ (petroleum ether/ethyl acetate 5:1)

Example IX (S)-4-(Bromomethyl)-3-chlorobenzenesulphonyl-N-2-(tertbutoxycarbonyl)pyrrolidinide

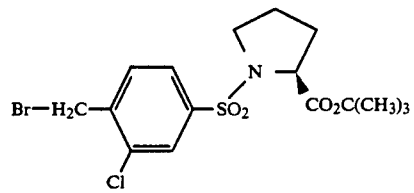

In analogy to the procedure of Example V, 13.9 g (96% of theory) of the title compound are obtained from 10.0 g (33 mmol) of the compound from Example IV and 5.7 g (33 mmol) of S-proline tert-butyl ester.

$R_f = 0.55$ (petroleum ether/ethyl acetate 7:3)

Example X rac-4-(Bromomethyl)-3-chlorobenzenesulphonyl-N-2-(tertbutoxycarbonyl)piperidinide

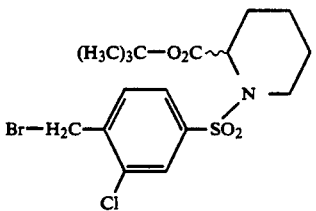

In analogy to the procedure of Example V, 14.6 g (98% of theory) of the title compound are obtained from 10.0 g (33 mmol) of the compound from Example IV and 6.1 g (33 mmol) of tert-butyl rac-pipecolate.

$R_f = 0.6$ (petroleum ether/ethyl acetate 7:3)

Example XI

6-Butyl-4-benzyloxycarbonyl-2-oxo-1,2-dihydropyridine

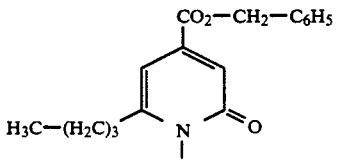

13.3 g (123 mmol) of benzyl alcohol and 4.7 g (31 mmol) of hydroxybenzotriazole are added to a solution of 6.0 g (31 mmol) of 6-butyl-2-oxo-1,2-dihydro-isonicotinic acid in 100 ml of DMF. The resulting clear solution is cooled to 0° C., followed by the addition of 7.0 g (34 mmol) of dicyclohexylcarbodiimide and 4.2 ml (31 mmol) of triethylamine. The mixture is allowed to thaw to 20° C., stirred for a further 2 hours and subjected to aqueous work-up. 6.8 g (77% of theory) of the title compound are obtained.

M.p.: 139° C.

Example XII

4-Methoxycarbonyl-2-oxo-6-propyl-1,2-dihydropyridine

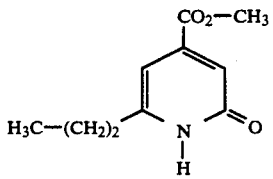

In analogy to the procedure of Example I, 13.7 g (88% of theory) of the title compound are obtained from 14.5 g (80 mmol) of 2-oxo-6-propyl-1,2-dihydro-isonicotinic acid and methanol.

M.p.: 144° C.

Example XIII

N-Trifluoroacetyl-L-prolinamide

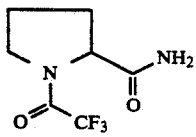

30 g (0.142 mol) of trifluoroacetylproline are initially introduced into 150 ml of DMF under protective gas. At −20° C., 142.6 ml (0.1704 mol) of 38% strength PPA in ethyl acetate are added. Ammonia is introduced until the mixture is saturated, a white precipitate depositing after 30 min. The batch is thawed under a gentle stream of ammonia. The whole reaction mixture is then added to 600 ml of H₂O and acidified to pH 4 with concentrated acetic acid. It is extracted 4× by shaking with 200 ml of methylene chloride and 3× by shaking with 200 ml of ether. The combined organic phases are dried using magnesium sulphate and the solvent is stripped off. The residues are chromatographed together on silica gel 60 F254 methylene chloride/methanol (10:1). The fractions containing the product are freed from solvent on a rotary evaporator.

17.12 g of the title compound (57% of theory) are obtained;

$R_f$: 0.345 (T/EA/CH₃COOH) 20:20:1.

Example XIV

2-Cyano-N-trifluororacetyl-pyrrolidine

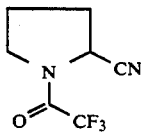

40 g (0.19 mol) of the products from Example XIII and 45 g=46 ml (0.57 mol) of pyridine are initially introduced into 300 ml of THF under protective gas. At 0° C., 48 g=32.25 ml (0.228 mol) of trifluoroacetic anhydride are added. The reaction mixture is stirred for 30 min at 0° C. and for 90 min at room temperature. The batch is then added to 1 l of 1N hydrochloric acid and extracted 3× by shaking with 200 ml of methylene chloride. The combined organic phases are extracted by shaking with 200 ml of saturated NaCl solution and dried over magnesium sulphate. The solvent is stripped off and the residue is chromatographed on silica gel 60 F254. Petroleum ether/ethyl acetate/acetic acid (1600:200:5). The fractions containing the products are concentrated. 32.4 g of the title compound (88.8% of theory) are obtained.

$R_f$: 0.57 (PE/EA 7:3).

Example XV

2-Tetrazolyl-N-trifluoroacetyl-pyrrolidine

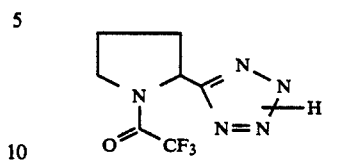

31.35 g=32.6 ml (0.26 mol) of diethylaluminium chloride are initially introduced into 65 ml of toluene under protective gas. 29.95 g =34.04 ml (0.26 mol) of trimethylsilyl azide are added at room temperature and the mixture is stirred for 10 min at room temperature. 25 g (0.13 mol) of the product from Example XIV, dissolved in 65 ml of toluene, are added at 0° C. The reaction mixture is stirred for 30 min at 0° C., 120 min at room temperature and 60 min at 40° C. The cooled batch is treated with saturated potassium fluoride solution until evolution of gas can no longer be detected.

The reaction mixture is added to 600 ml of H₂O and acidified to pH 4 and extracted 3× with 100 ml of ethyl acetate. The combined organic phases are treated with 50 ml of n-hexane. In order to remove the azides, about ⅓ of the solvent is removed by distillation over a distillation bridge without cooling. The residue is dried over magnesium sulphate and freed from solvent on a rotary evaporator.

18.54 g of the title compound (60.6% of theory) are obtained.

$R_f$: 0.4 (toluene/ethyl acetate 1:1).

Example XVI

N-Trifluoroacetyl-2-[N-trityl-tetrazolyl]pyrrolidine

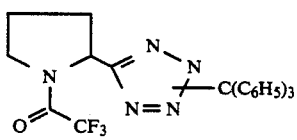

16.23 g (0.069 mol) of the product from Example XV and 10.47 g=14.35 ml (0.1035 mol) of triethylamine are initially introduced into 70 ml of methylene chloride. 19.83 g (0.069 mol) of triphenylmethyl chloride are then added. The reaction mixture is stirred for 1.5 h at room temperature, diluted with methylene chloride and extracted with pH 5 buffer solution (3×50 ml). The organic phase is dried over magnesium sulphate. The solvent is stripped off on a rotary evaporator. The residue is stirred with ether. The resulting crystals are filtered off with suction and dried.

24.65 g of the title compound (75% of theory) are obtained.

$R_f$: 0.53 (petroleum ether/ethyl acetate 7:3).

Example XVII 2-(N-Trityl-tetrazolyl)pyrrolidine

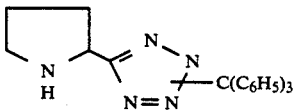

24 g (0.05 mol) of the product from Example XVI are initially introduced into 100 ml of ethanol under protective gas. 2.84 g (0.075 mol) of sodium borohydride are added in portions at 0° C. The batch is thawed and stirred at room temperature for 1 h. It is treated with 6 ml of acetic acid and the whole reaction mixture is added to 500 ml of buffer solution pH 9. The batch is extracted with 3×75 ml of methylene chloride. The combined organic phases are dried over magnesium sulphate and freed from solvent on a rotary evaporator. The residue is chromatographed on silica gel 60 F254. Petroleum ether/ethyl acetate (7:3). The corresponding fractions are concentrated and dried.

7.16 g of the title compound (37.5% of theory) are obtained.

$R_f$: 0.22 (ethyl acetate).

Example XVIII

4-Bromomethyl-3-chloro-benzenesulphonic acid-2-[trityltetrazolyl]pyrrolidinide

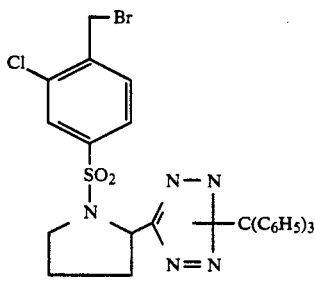

In analogy to the procedure of Example III, 6.49 g of the title compound (95% of theory) are obtained from 3.19 g (10.5 mmol) of the compound from Example IV and 4 g (10.5 mmol) of the compound from Example XVII.

$R_f$: 0.53 (petroleum ether/ethyl acetate 7:3).

Example XIX 4-(Bromomethyl)-3-fluorobenzenesulphochloride

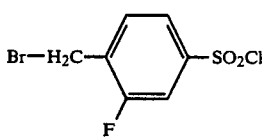

20.9 g (0.1 mol) of 3-fluoro-4-methylbenzenesulphochloride are taken up in 200 ml of carbon tetrachloride and, after addition of 19.6 g (0.11 mol) of N-bromosuccinimide and 0.3 g of dibenzoyl peroxide, the mixture is heated under reflux for 5 h. After cooling, the solids are filtered off and the filtrate is freed from solvent. Flash chromatography petroleum ether/toluene (4:1), 50 μm particle size gives 12.4 g (44% of theory) of the title compound $R_f$: 0.42 (petroleum ether/toluene 3:1).

Example XX 4-(Bromomethyl)-3-trifluoromethylbenzenesulphochloride

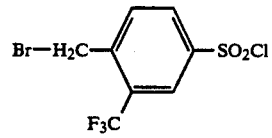

64.6 g (0.25 mol) of 3-trifluoromethyl-4-methylbenzenesulphochloride are taken up in 500 ml of carbon tetrachloride and, after addition of 44.5 g (0.25 mol) of N-bromosuccinimide and 0.4 g of ABN, the mixture is heated under reflux for 24 h. After cooling, the solids are filtered off and the filtrate is freed from solvent. Flash chromatography petroleum ether/toluene (4:1), 50 μm particle size gives 33.9 g (40% of theory) of the title compound.

$R_f$: 0.41 (petroleum ether/toluene 3:1)

Example XXI (S)-4-(Bromomethyl)-3-fluorobenzenesulphonyl-N-2-(tertbutoxy-carbonyl)pyrrolidinide

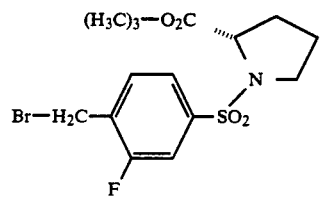

In analogy to the procedure of Example III, 12.7 g (100% of theory) of the title compound are obtained from 8.6 g (30 mmol) of the compound from Example XIX and 5.1 g (30 mmol) of S-proline tert-butyl ester.

$R_f$: 0.57 (petroleum ether/ethyl acetate 7:3).

Example XXII (S)-4-(Bromomethyl)-3-trifluoromethylbenzenesulphonyl-N-2-(tert-butoxycarbonyl-pyrrolidinide

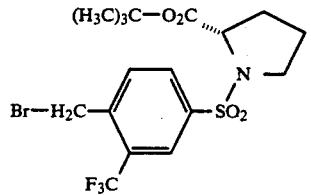

In analogy to the procedure of Example III, 23.6 g (100% of theory) of the title compound are obtained from 16.9 g (50 mmol) of the compound from Example XX and 8.6 g (50 mmol) of S-proline tert-butyl ester.

$R_f$: 0.63 (petroleum ether/ethyl acetate 7:3).

Example XXIII (S)-4-carboxy-3-hydroxybenzenesulphonyl-N-2-(tert.-butoxycarbonyl)-pyrrolidinide

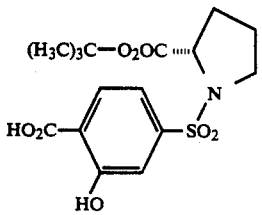

Analogously to the method of Example V 300 g (81% of theory) of the title compound are obtained from 23.7 g of 4-carboxy-3-hydroxybenzenesulphochloride (100 mmol) and 17 g (100 mmol) of S-proline tert.-butyl ester.

$R_f$: 0.18 (acetone)

Example XXIV (S)-4-Benzyloxycarbonyl-3-benzyloxybenzenesulphonic acid N-2-(tert.-butoxycarbonyl)-pyrrolidinide

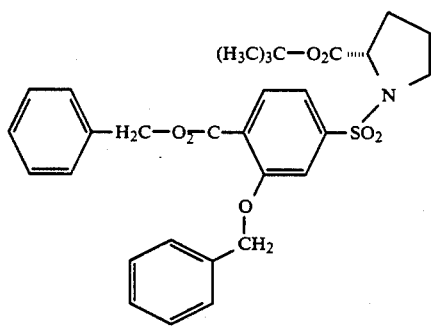

28.3 g of $K_2CO_3$ (204 mmol) and 25.7 g (150 mmol) of benzyl bromide are added to 25.3 g (68 mmol) of the compound of Example XXIII dissolved in 200 ml of DMF. The reaction mixture is stirred for a further 2 hours at 75° C. and cooled. 1 l of water is then added and the mixture is extracted with ethyl acetate (3×400 ml) and the extract washed with water (5×400 ml), dried over $MgSO_4$, filtered and all the volatile components are stripped off in vacuo. The product is purified by flash chromatography (petroleum ether/$CH_2Cl_2$ 5:1 and petroleum ether/ethyl acetate 6:1, particle size: 50μ) and then purified further by recrystallisation from 600 ml of a solvent mixture (petroleum ether/ethyl acetate 6:1). 35.5 g (95% of theory) of the title compound are obtained.

$R_f$=0.53 (petroleum ether/ethyl acetate 7:3)

Example XXV (S)-4-(Hydroxymethyl)-3-benzyloxybenzenesulphonic acid N-2-(tert.-butoxycarbonyl)-pyrrolidinide

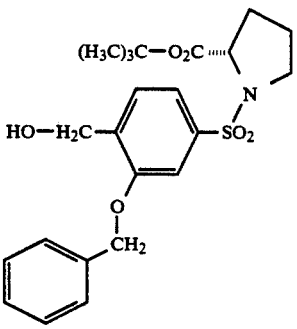

11.03 g (20 mmol) of the compound of Example XXIV are dissolved in 100 ml of diglyme and, after adding 1.51 g (40 mmol) of sodium borohydride and 1.68 g (40 mmol) of LiCl, the mixture is stirred for 4 hours at 70° C. After cooling, 500 ml of water are added to the reaction mixture, which is then acidified with 1N HCl to a pH of 3. The mixture is extracted with ether (3×300 ml) and the extract is washed with water (6×300 ml), dried over $MgSO_4$ and the filtrate freed from the solvent. The residue is chromatographed on silica gel 60 F 254 (petroleum ether/ethyl acetate (7:3)). The corresponding fractions are concentrated by evaporation and dried. 5.0 g (56% of theory) of the title compound are obtained.

$R_f$=0.36 (petroleum ether/ethyl acetate 7:3)

Example XXVI (S)-4-(Bromomethyl)-3-benzyloxybenzenesulphonic acid N-2-(tert.-butoxycarbonyl)-pyrrolidinide

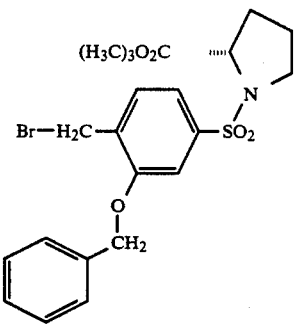

2.24 g (5 mmol) of the compound from Example XXV are initially introduced into 20 ml of absolute DMF under an inert gas. 2.53 g (6 mmol) of triphenylphosphine dribromide are added at 0° C. The reaction mixture is stirred for 1 hour at room temperature. 200 ml of water are added, the mixture is extracted with ethyl acetate (3×80 ml) and the extract is washed with water (5×60 ml), dried over $MgSO_4$, filtered and all the volatile components are stripped off in vacuo. The product is purified by flash chromatography ($CH_2Cl_2$, particle size: 50μ) and 2.55 g (100% of theory) of the title compound are obtained.

$R_f$=0.56 (petroleum ether/ethyl acetate 7:3)

PREPARATION EXAMPLES

Example 1 rac-4-[4-Benzyloxycarbonyl-6-butyl-2-oxo-1,2-dihydropyridin-1-yl]-methyl-3-chloro-benzenesulphonyl-N-(2-tert-butoxycarbonyl)piperidinide

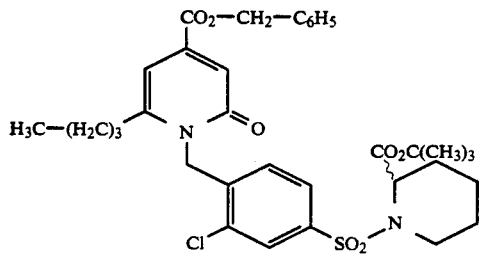

500 mg (1.75 mmol) of the product from Example X and 570 mg (1.75 mmol) of $Cs_2CO_3$ are suspended in 10 ml of dry 1,2-dimethoxyethane and stirred at 20° C. for 10 min. 790 mg (1.75 mmol) of the product from Example VII, dissolved in 10 ml of 1,2-dimethoxyethane, are added and the mixture is stirred at 20° C. for 5 h. The reaction mixture is cooled, added to 100 ml of $H_2O$, extracted with ethyl acetate (4×60 ml) and dried over $MgSO_4$, and the solvent is stripped off in vacuo. The crude product is chromatographed on silica gel (50μ particle size, eluent petroleum ether/ethyl acetate 10:1 → 7:3). 78 mg (8% of theory) of the title compound are obtained.

$R_f$: 0.09 (petroleum ether/ethyl acetate 5:1)

Example 2 rac-4-[4-Benzyloxycarbonyl-6-butyl-2-oxo-1,2-dihydropyridin-1-yl]methyl-3-chloro-benzenesulphonyl-N-(2-carboxy)piperidinide

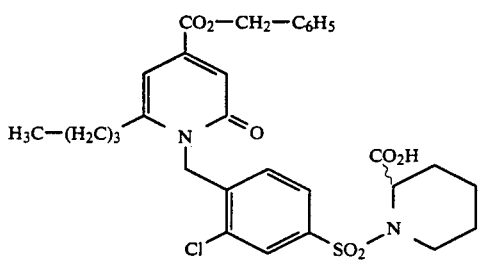

400 ml of trifluoroacetic acid are added to a solution of 76 mg (126 μmol) of the compound from Example 1 in 2 ml of dichloromethane and the mixture is stirred at 20° C. for 5 h. It is diluted with 10 ml of dichloromethane, washed with water (4×20 ml) and saturated NaCl solution (1×20 ml) and dried over $MgSO_4$, and the solvent is stripped off in vacuo. The residue is purified by flash chromatography on 20 g of silica gel (50μ particle size, eluent: toluene/ethyl acetate/trifluoroacetic acid 10:40:1). 63 mg (83% of theory) of the title compound are obtained.

$R_f$=0.66 (dichloromethane/methanol 10:1)

Example 3 rac-4-[6-Butyl-4-carboxy-2-oxo-1,2-dihydropyridin-1-yl]methyl-3-chloro-benzenesulphonyl-N-(2-carboxy)piperidinide

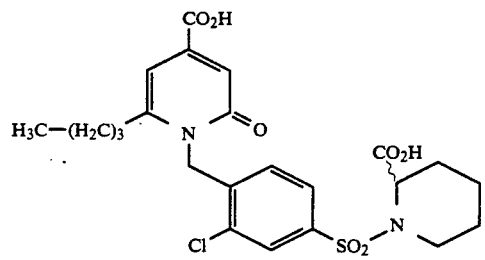

58 mg (96 μmol) of the compound from Example 1 are dissolved in 0.5 ml of THF, 0.5 ml of $H_2O$ and 0.1 ml of $CH_3OH$. After addition of 12 mg (129 μmol) of LiOH, the solution is stirred at RT for 2.5 h. The solution is concentrated, treated with $H_2O$ and ethyl acetate and acidified to pH=3 with acetic acid. The phases are separated and the aqueous phase is additionally extracted three times with ethyl acetate. The combined organic phases are washed with water (7×20 ml) and saturated NaCl solution (1×20 ml), dried over $MgSO_4$ and concentrated. 36 mg (74%) of the title compound are obtained.

$R_f$=0.16 (dichloromethane/methanol 10:1).

The compounds shown in Table 1 are prepared in analogy to the procedures of Preparation Examples 1–3:

TABLE 1

[Structure: pyridin-2-one with R3 at 4-position, R1 at 6-position, N-CH2-phenyl where phenyl has R5 ortho and SO2A para]

| Ex. No. | R¹ | R³ | R⁵ | A | $R_f$* |
|---|---|---|---|---|---|
| 4 | —(CH₂)₃—CH₃ | —CO₂CH₂C₆H₅ | Cl | pyrrolidine-N-, 2-CO₂C(CH₃)₃ | 0.9[a] |
| 5 | —(CH₂)₃—CH₃ | —CO₂CH₂C₆H₅ | Cl | pyrrolidine-N-, 2-CO₂H | 0.52[a] |
| 6 | —(CH₂)₃—CH₃ | —CO₂H | Cl | pyrrolidine-N-, 2-CO₂H | 0.14[a] |
| 7 | —(CH₂)₃—CH₃ | —CO₂CH₃ | H | pyrrolidine-N-, 2-CO₂C(CH₃)₃ | |
| 8 | —(CH₂)₃—CH₃ | —CO₂CH₃ | H | pyrrolidine-N-, 2-CO₂H | |
| 9 | —(CH₂)₃—CH₃ | —CO₂H | H | pyrrolidine-N-, 2-CO₂H | |
| 10 | —(CH₂)₂—CH₃ | —CO₂CH₃ | H | piperidine-N-, 2-CO₂C(CH₃)₃ | 0.35[a] |
| 11 | —(CH₂)₂—CH₃ | —CO₂CH₃ | H | piperidine-N-, 2-CO₂H | 0.36[a] |
| 12 | —(CH₂)₃—CH₃ | —CO₂CH₃ | H | piperidine-N-, 2-HO₂C | 0.42[a] |

TABLE 1-continued

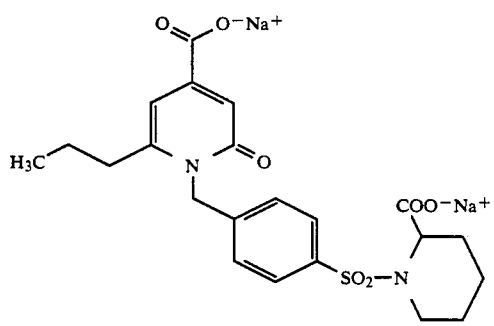

| Ex. No. | R¹ | R³ | R⁵ | A | $R_f{}^*$ |
|---|---|---|---|---|---|
| 13 | —(CH₂)₃—CH₃ | —CO₂H | H | HO₂C–[piperidin-2-yl, N-attached] | 0.34[b] |
| 14 | —(CH₂)₃—CH₃ | —CO₂Me | Cl | (S)-2-carboxy-pyrrolidin-1-yl | 0.60[a] |

Example 15

Di-sodium rac-4-[6-butyl-4-carboxy-2-oxo-1,2-dihydropyridin-1-yl]-4-methyl-benzenesulphonyl-N-(2-carboxy)piperdinide

[Structure: 6-propyl-4-(CO₂⁻Na⁺)-2-oxo-1,2-dihydropyridine N-substituted with a 4-(piperidine-2-carboxylate sodium)sulfonyl-benzyl group]

120 mg (0.25 mmol) of the compound from Example 11 are treated in 5 ml of THF and 2.5 ml of water with 0.25 ml of 1N sodium hydroxide solution for 1 hour at room temperature, the reaction solution is concentrated and the residue is dried over P₂O₅ in a high vacuum.

Yield: 115 mg (91% of theory)

$R_f$ = 0.28[b]

The compounds shown in Table 2 are prepared by the use of 1 mol equivalent of NaOH in analogy to the procedure of Example 14.

TABLE 2

[Same core structure as Table 1]

| Ex. No. | R¹ | R³ | R⁵ | A | $R_f{}^*$ |
|---|---|---|---|---|---|
| 16 | —(CH₂)₂—CH₃ | —CO₂CH₃ | H | 2-(CO₂⁻Na⁺)-piperidin-1-yl | 0.36[a] |

TABLE 2-continued

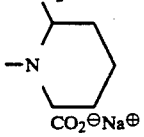

| Ex. No. | R¹ | R³ | R⁵ | A | R_f* |
|---|---|---|---|---|---|
| 17 | —(CH₂)₃—CH₃ | —CO₂CH₃ | H | 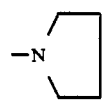 | 0.42ᵃ⁾ |
| 18 | —(CH₂)₃—CH₃ | —CO₂CH₃ | H | 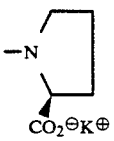 | 0.22ᶜ⁾ |
| 19 | —(CH₂)₃—CH₃ | —CO₂Me | Cl | 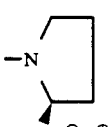 | 0.60ᵃ⁾ |
| 20 | —(CH₂)₃—CH₃ | —CO₂H | Cl | 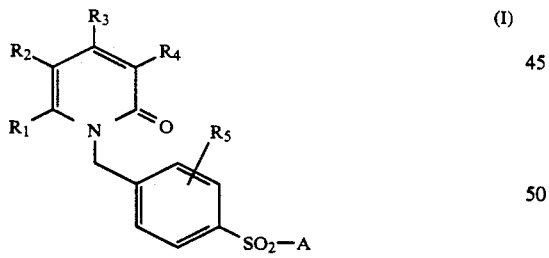 | |

We claim:

1. A sulphonylbenzyl-substituted pyridone of the formula

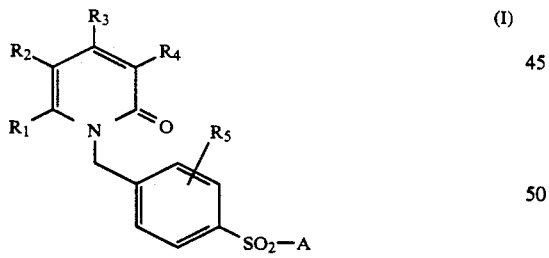

(I)

in which

R¹ represents straight-chain or branched alkyl having up to 8 carbon atoms, which is optionally substituted by cycloalkyl having 3 to 6 carbon atoms, hydroxyl or by straight-chain or branched alkoxy having up to 6 carbon atoms, or represents cycloalkyl having 3 to 6 carbon atoms, R², R³ and R⁴ are identical or different and represent hydrogen, cyano or straight-chain or branched perfluoroalkyl having up to 8 carbon atoms, or represent straight-chain or branched alkyl having up to 8 carbon atoms, which is optionally monosubstituted or disubstituted by identical or different substituents from the group consisting of hydroxyl, halogen, carboxyl, and straight-chain or branched alkoxy or alkoxycarbonyl each having up to 6 carbon atoms, or by phenyl, phenoxy or by a 5- to 7-membered, saturated or unsaturated heterocycle having up to three heteroatoms, where the cyclic systems can in turn be monosubstituted or disubstituted by identical or different substituents from the group consisting of trifluoromethyl, trifluoromethoxy, halogen, nitro, cyano, hydroxyl and hydroxymethyl or by straight-chain or branched alkyl or alkoxy each having up to 6 carbon atoms, or represent straight-chain or branched acyl or alkoxycarbonyl each having up to 8 carbon atoms, benzyloxycarbonyl or carboxyl, or represent phenyl which is optionally monosubstituted to trisubstituted by identical or different substitutents from the group consisting of halogen, nitro, cyano, hydroxyl, hydroxymethyl, trifluoromethyl and trifluoromethoxy or by straight-chain or branched alkyl or alkoxy each having up to 6 carbon atoms, or represent a group of the formula —CO—NR⁶R⁷, in which R⁶ and R⁷ are identical or different and denote hydrogen, straight-chain or branched alkyl having up to 8 carbon atoms or aryl or aralkyl each having 6 to 10 carbon atoms, R⁵ represents hydrogen, halogen or straight-chain or branched alkyl having up to 8 carbon atoms, or represents straight-chain or branched perfluoroalkyl having up to 6 carbon atoms, or represents a group of the formula —OX, wherein X denotes hydrogen, benzyl, a hydroxyl protective group or denotes straight-chain or branched alkyl having up to 8 carbon atoms, A represents a 3 to 8-membered saturated nitrogen containing heterocycle bonded via a nitrogen atom and having up to 2 further heteroatoms from the series consisting of S, N and O and which is optionally monosubstituted or disubstituted by identical or different substituents from the group consisting of perfluoroalkyl having up to 5 carbon atoms and a radical of the formula

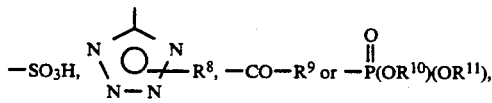

$-SO_3H$, $\begin{matrix} N \\ \diagdown \\ N-N \end{matrix} \begin{matrix} \diagup \\ O \\ \diagdown \end{matrix} R^8$, $-CO-R^9$ or $-\overset{O}{\underset{\|}{P}}(OR^{10})(OR^{11})$, in which $R^8$ denotes hydrogen, straight-chain or branched alkyl having up to 6 carbon atoms or triphenylmethyl $R^9$ denotes hydroxyl, straight-chain or branched alkoxy having up to 8 carbon atoms, phenoxy, benzyloxy or a group of the formula $-NR^{12}R^{13}$, in which $R^{12}$ and $R^{13}$ are identical or different and denote hydrogen or straight-chain or branched alkyl having up to 6 carbon atoms or phenyl, $R^{10}$ and $R^{11}$ are identical or different and denote hydrogen, straight-chain or branched alkyl having up to 8 carbon atoms or phenyl, and their salts.

2. A sulphonylbenzyl-substituted pyridone according to claim 1, in which $R^1$ represents a straight-chain or branched alkyl each having up to 6 carbon atoms, which is optionally substituted by cyclopropyl, cyclopentyl, cyclohexyl, hydroxyl or by straight-chain or branched alkoxy having up to 4 carbon atoms, or represents cyclopropyl, cyclopentyl or cyclohexyl, $R^2$, $R^3$ and $R^4$ are identical or different and represent hydrogen, cyano or straight-chain or branched perfluoroalkyl having up to 6 carbon atoms, or represent straight-chain or branched alkyl having up to 6 carbon atoms, which is substituted by hydroxyl, fluorine, chlorine, bromine, carboxyl, straight-chain or branched alkoxy or alkoxycarbonyl each having up to 4 carbon atoms, or by phenyl, phenoxy or thienyl, where the cyclic systems can in turn be substituted by trifluoromethoxy, trifluoromethyl, hydroxymethyl, fluorine, chlorine, bromine or by straight-chain or branched alkyl or alkoxy each having up to 6 carbon atoms, or represent straight-chain or branched acyl or alkoxycarbonyl each having up to 6 carbon atoms, benzyloxycarbonyl or carboxyl, or represent phenyl which is optionally monosubstituted or disubstituted by identical or different substituents from the group consisting of fluorine, chlorine, bromine, trifluoromethyl, trifluoromethoxy and hydroxymethyl or by straight-chain or branched alkyl or alkoxy each having up to 4 carbon atoms, or represent a group of the formula $-CONR^6R^7$, in which $R^6$ and $R^7$ are identical or different and denote hydrogen, straight-chain or branched alkyl having up to 6 carbon atoms, phenyl or benzyl, $R^5$ represents hydrogen, fluorine, chlorine, bromine, or straight-chain or branched alkyl having up to 6 carbon atoms, or represents straight-chain or branched perfluoroalkyl having up to 4 carbon atoms, or represents a group of the formula —OX, wherein X denotes hydrogen, benzyl, acetyl, or denotes straight-chain or branched alkyl having up to 6 carbon atoms, A represents piperidyl, pyrrolidinyl or morpholinyl bonded via the nitrogen atom, each of which is optionally substituted by trifluoromethyl or by a radical of the formula

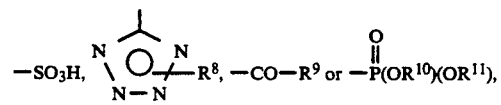

$-SO_3H$, $\begin{matrix} N \\ \diagdown \\ N-N \end{matrix} \begin{matrix} \diagup \\ O \\ \diagdown \end{matrix} R^8$, $-CO-R^9$ or $-\overset{O}{\underset{\|}{P}}(OR^{10})(OR^{11})$, in which $R^8$ denotes hydrogen, straight-chain or branched alkyl having up to 4 carbon atoms or triphenylmethyl, $R^9$ denotes hydroxyl, straight-chain or branched alkoxy having up to 6 carbon atoms, phenoxy, benzyloxy or a group of the formula $-NR^{12}R^{13}$, in which $R^{12}$ and $R^{13}$ are identical or different and denote hydrogen or straight-chain or branched alkyl having up to 4 carbon atoms, and $R^{10}$ and $R^{11}$ are identical or different and denote hydrogen, straight-chain or branched alkyl having up to 6 carbon atoms or phenyl, and their salts.

3. A sulphonylbenzyl-substituted pyridone according to claim 1, in which $R^1$ represents straight-chain or branched alkyl having up to 4 carbon atoms, which is optionally substituted by cyclopropyl or represents cyclopropyl, $R^2$, $R^3$ and $R^4$ are identical or different and represent hydrogen, cyano or straight-chain or branched perfluoroalkyl having up to 4 carbon atoms, represent straight-chain or branched alkyl having up to 4 carbon atoms, which is substituted by hydroxyl or straight-chain or branched alkoxy or alkoxycarbonyl each having up to 3 carbon atoms, or represent straight-chain or branched acyl or alkoxycarbonyl each having up to 4 carbon atoms, benzyloxycarbonyl or carboxyl, or represent a group of the formula $-CONR^6R^7$, in which $R^6$ and $R^7$ are identical or different and denote hydrogen, straight-chain or branched alkyl having up to 4 carbon atoms, phenyl or benzyl, $R^5$ represents hydrogen, fluorine, chlorine, straight-chain or branched alkyl having up to 4 carbon atoms, or represents straight-chain or branched perfluoroalkyl having up to 3 carbon atoms, or represents a group of the formula —OX, wherein X denotes hydrogen, benzyl, acetyl or denotes straight-chain or branched alkyl having up to 6 carbon atoms.

A represents piperidyl or pyrrolidinyl bonded via the nitrogen atom, each of which is optionally substituted by trifluoromethyl or by a radical of the formula

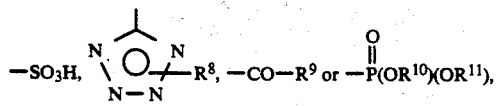

in which

R[8] denotes hydrogen, methyl, ethyl or triphenylmethyl,

R[9] denotes hydroxyl, straight-chain or branched alkoxy having up to 4 carbon atoms, phenoxy, benzyloxy or a group of the formula $-NR^{12}R^{13}$, in which R[12] and R[13] are identical or different and denote hydrogen or straight-chain or branched alkyl having up to 3 carbon atoms and R[10] and R[11] are identical or different and denote hydrogen, straight-chain or branched alkyl having up to 4 carbon atoms or phenyl, and their salts.

4. A compound according to claim 1, wherein such compound is 4-[6-butyl-4-carboxy-2-oxo-1,2-dihydropyridin-1-yl]methyl-(3-chloro-benzenesulphonyl-N-(2-carboxy)pyrrolidinide of the formula

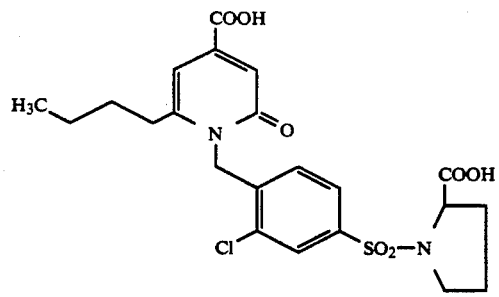

or a salt thereof.

5. A compound according to claim 1, wherein such compound is 4-[6-butyl-4-methoxycarbonyl-2-oxo-1,2-dihydropyridin-1-yl]methyl-(3-chlorobenzene-sulphonyl-N-(2-carboxy)pyrrolidinide of the formula

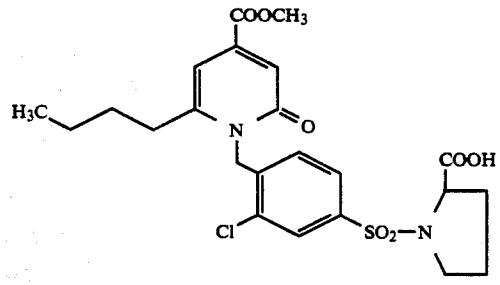

or a salt thereof.

6. A composition for the treatment of arterial hypertension and atherosclerosis comprising an amount effective therefor of a compound or salt thereof according to claim 1 and a pharmacologically acceptable diluent.

7. The method of treating arterial hypertension and atherosclerosis in a patient in need thereof which comprises administering to such patient an amount effective therefor of a compound and salt thereof according to claim 1.

* * * * *